`US008133960B2`

(12) United States Patent
Linhardt et al.

(10) Patent No.: US 8,133,960 B2
(45) Date of Patent: Mar. 13, 2012

(54) BIOMEDICAL DEVICES

(75) Inventors: Jeffrey G. Linhardt, Fairport, NY (US); Joseph A. McGee, Canandaigua, NY (US); Ivan M. Nunez, Penfield, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 310 days.

(21) Appl. No.: 12/456,421

(22) Filed: Jun. 16, 2009

(65) Prior Publication Data
US 2010/0317817 A1  Dec. 16, 2010

(51) Int. Cl.
C08F 226/06 (2006.01)
C08F 30/08 (2006.01)
C08F 12/30 (2006.01)
C08G 75/00 (2006.01)

(52) U.S. Cl. ........ 526/263; 526/279; 526/286; 526/288; 526/319; 528/390

(58) Field of Classification Search .................. 526/263, 526/279, 286, 319, 288; 528/390
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deichert et al. | |
| 4,197,266 A | 4/1980 | Clark et al. | |
| 4,327,203 A | 4/1982 | Deichert et al. | |
| 4,355,147 A | 10/1982 | Deichert et al. | |
| 4,555,732 A | 11/1985 | Tuhro | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Nandu et al. | |
| 5,270,418 A | 12/1993 | Kunzler et al. | |
| 5,271,875 A | 12/1993 | Appleton et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 6,440,571 B1 | 8/2002 | Valint, Jr. et al. | |
| 6,902,812 B2 | 6/2005 | Valint, Jr. et al. | |
| 2004/0138323 A1* | 7/2004 | Stenzel-Rosebaum et al. | 521/142 |
| 2007/0197733 A1* | 8/2007 | Salamone et al. | 525/242 |
| 2008/0124378 A1* | 5/2008 | Byrne et al. | 424/429 |

FOREIGN PATENT DOCUMENTS

| | | |
|---|---|---|
| WO | WO 96/31792 | 10/1996 |
| WO | WO2009/085819 A1 | 7/2009 |

OTHER PUBLICATIONS

Karunakaran et al. "Synthesis, Characterization, and Crosslinking of Methacrylate-Telechelic PDMAAm-b-PDMS-b-PDMAAm Copolymers", Published online in Wiley InterScience (www.interscience.wiley.com), Apr. 17, 2007.*
International Search Report (PCT/ISA/210) and Written Opinion (PCT/ISA/237) mailed on Dec. 28, 2010.
Pai, T S C et al. "Synthesis of Amphiphilic Block Copolymers based on poly(dimethylsiloxane) via fragmentation . . . " in J. Polymer, vol. 45, No. 13, Jun. 1, 2004, pp. 4383-4389.
Pavlovic, D et al. "Synthesis of amphiphilic multiblock and triblock copolymers of polydimethylsiloxane . . . " in J. Polym. Sci., vol. 46, No. 21, Nov. 1, 2008, pp. 7033-7048.
Karunakaran R et al. "Synthesis, characterization, and crosslinking of methacrylate-telechelic.." in J. Polym Sci, Part A, vol. 45, #18, Sep. 15, 2007, pp. 4284-4290, XP002537457.
Valint P L et al. "Surface-Active Macromonomers for Coating of Contact Lens Polymers" in Polymeric Materials Sci and Eng, vol. 76, Apr. 13, 1997, pp. 93-94, XP000931173.
Wan et al. "Xanthate-mediated Radical Polymerization of N-vinylpyrrolidone . . . " in Macromolecules, vol. 38, No. 25, Dec. 13, 2005, pp. 10397-10405, XP002612624.
Lowe et al. "Reversible Addition-fragmentation Chain Transfer . . . " in Polymer Science, vol. 32, No. 3, Mar. 2, 2007, pp. 283-351, XP005911232.
Lai, Yu-Chin, "The Role of Bulky Polysiloxanylalkyl Methacrylates in Polyurethane-Polysiloxane Hydrogels," Journal of Applied Polymer Science, vol. 60, 1193-1199 (1996).
U.S. Appl. No. 61/113,736, filed Nov. 12, 2008, McGee.
U.S. Appl. No. 61/113,739, filed Nov. 12, 2008, McGee.
U.S. Appl. No. 61/113,742, filed Nov. 12, 2008, Nunez.
U.S. Appl. No. 61/113,746, filed Nov. 12, 2008, Nunez.

* cited by examiner

*Primary Examiner* — Michael M Bernshteyn
(74) *Attorney, Agent, or Firm* — Glenn D. Smith; M. Carmen & Associates, PLLC

(57) ABSTRACT

Biomedical devices such as contact lenses formed from a polymerization product of a mixture comprising (a) a random copolymer comprising hydrophilic units and hydrophobic units, wherein the random copolymer has at least one thio carbonyl thio fragment of a reversible addition fragmentation chain transfer ("RAFT") agent are disclosed.

24 Claims, No Drawings

BIOMEDICAL DEVICES

BACKGROUND OF THE INVENTION

1. Technical Field

The present invention generally relates to biomedical devices such as ophthalmic lenses.

2. Description of Related Art

Biomedical devices such as contact lenses are made of various polymeric materials, including rigid gas permeable materials, soft elastomeric materials, and soft hydrogel materials. The majority of contact lenses sold today are made of soft hydrogel materials. Hydrogels are a cross-linked polymeric system that absorb and retain water, typically 10 to 80 percent by weight, and especially 20 to 70 percent water. Hydrogel lenses are commonly prepared by polymerizing a lens-forming monomer mixture including at least one hydrophilic monomer, such as 2-hydroxyethyl methacrylate, N,N-dimethylacrylamide, N-vinyl-2-pyrrolidone, glycerol methacrylate, and methacrylic acid. In the case of silicone hydrogel lenses, a silicone-containing monomer is copolymerized with the hydrophilic monomers. Regardless of their water content, both hydrogel and non-hydrogel siloxy and/or fluorinated contact lenses tend to have relatively hydrophobic, non-wettable surfaces.

In the field of biomedical devices such as contact lenses, various physical and chemical properties such as, for example, oxygen permeability, wettability, material strength and stability are but a few of the factors that must be carefully balanced in order to provide a useable contact lens. For example, since the cornea receives its oxygen supply from contact with the atmosphere, good oxygen permeability is an important characteristic for certain contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

It is known that increasing the hydrophilicity of a contact lens surface improves the wettability of the contact lenses. This, in turn, is associated with improved wear comfort of the lens. Additionally, the surface of the lens can affect the overall susceptibility of the lens to deposition of proteins and lipids from the tear fluid during lens wear. Accumulated deposits can cause eye discomfort or even inflammation. In the case of extended wear lenses, i.e., a lens used without daily removal before sleep, the surface is especially important, since extended wear lenses must be designed for high standards of comfort and biocompatibility over an extended period of time. Accordingly, new formulations that have the potential to yield improved surface qualities are still desirable.

It would therefore be desirable to provide improved biomedical devices such as contact lenses that exhibit suitable physical and chemical properties, e.g., oxygen permeability, lubriciousness and wettability, for prolonged contact with the body while also being biocompatible. It would also be desirable to provide improved biomedical devices that are easy to manufacture in a simple, cost effective manner.

SUMMARY OF THE INVENTION

In accordance with one embodiment of the present invention, a biomedical device is provided comprising a polymerization product of a mixture comprising (a) a random copolymer comprising hydrophilic units and hydrophobic units, wherein the random copolymer has at least one thio carbonyl thio fragment of a reversible addition fragmentation chain transfer ("RAFT") agent.

In accordance with a second embodiment of the present invention, an ophthalmic lens is provided comprising a polymerization product of a mixture comprising (a) a random copolymer comprising hydrophilic units and hydrophobic units, wherein the random copolymer has at least one thio carbonyl thio fragment of a RAFT agent.

The biomedical devices of the present invention are advantageously formed from a random copolymer comprising hydrophilic units and hydrophobic units, wherein the random copolymer has at least one thio carbonyl thio fragment of a RAFT agent. The random copolymers comprising hydrophilic units and hydrophobic units, wherein the random copolymer has at least one thio carbonyl thio fragment of a RAFT agent are capable of forming biomedical devices with a hydrophilic or lubricious (or both) surface. Hydrophilic and/or lubricious surfaces of the biomedical devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer. In addition, the lens will not dry out as rapidly, thereby further improving the comfort level for the wearer.

DETAILED DESCRIPTION OF THE PREFERRED EMBODIMENTS

The present invention is directed to biomedical devices intended for direct contact with body tissue or body fluid. As used herein, a "biomedical device" is any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The preferred biomedical devices are ophthalmic devices, particularly contact lenses, and most particularly contact lenses made from hydrogels.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

The biomedical devices of the present invention are formed from a polymerization product of a mixture comprising a random copolymer comprising hydrophilic units and hydrophobic units, wherein the random copolymer has at least one thio carbonyl thio fragment of a RAFT agent. The random copolymers comprising one or more hydrophilic units and hydrophobic units, and at least one thio carbonyl thio fragment of a RAFT agent are prepared via RAFT polymerization, i.e., monomers are polymerized via a RAFT mechanism. RAFT polymerization is a radical polymerization technique capable of preparing random copolymers having a well defined molecular architecture and low polydispersity.

The RAFT agents suitable for use herein are based upon thio carbonyl thio chemistry which is well known to those of ordinary skill in the art. The thio carbonyl thio fragment can be derived from a RAFT agent such as, for example, a xanthate-containing compound, trithiocarbonate-containing compound, dithiocarbamate-containing compound or dithio ester-containing compound, wherein each compound contains a thio carbonyl thio group. One class of RAFT agents that can be used herein is of the general formula:

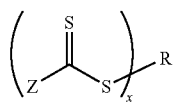

wherein x is 1 or 2, Z is a substituted oxygen (e.g., xanthates (—O—R)), a substituted nitrogen (e.g., dithiocarbamates (—NRR)), a substituted sulfur (e.g., trithiocarbonates (—S—R)), a substituted or unsubstituted $C_1$-$C_{20}$ alkyl or $C_3$-$C_{25}$ unsaturated, or partially or fully saturated ring (e.g., dithioesters (—R)) or carboxylic acid-containing group; and R is independently a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a $C_1$-$C_{20}$ ester group; an ether or polyether-containing group; an alkyl- or arylamide group; an alkyl- or arylamine group; a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; a substituted or unsubstituted $C_6$-$C_{30}$ heteroarylalkyl group; and combinations thereof.

Representative examples of alkyl groups for use herein include, by way of example, a straight or branched alkyl chain radical containing carbon and hydrogen atoms of from 1 to about 30 carbon atoms and preferably from 1 to about 12 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of cycloalkyl groups for use herein include, by way of example, a substituted or unsubstituted non-aromatic mono or multicyclic ring system of about 3 to about 30 carbon atoms and preferably from 3 to about 6 carbon atoms such as, for example, cyclopropyl, cyclobutyl, cyclopentyl, cyclohexyl, perhydronaphthyl, adamantyl and norbornyl groups, bridged cyclic groups or spirobicyclic groups, e.g., spiro-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms and preferably from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms and preferably from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronaphthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$(R^2OR^3)_t$, wherein $R^2$ is a bond, a substituted or unsubstituted alkyl, cycloalkyl or aryl group as defined herein and $R^3$ is a substituted or unsubstituted alkyl, cycloalkyl or aryl group as defined herein and t is at least 1, e.g., —$CH_2CH_2OC_6H_5$ and $CH_2$—$CH_2$—$CH_2$—O—$CH_2$—$(CF_2)_z$—H where z is 1 to 6, —$CH_2CH_2OC_2H_5$, and the like.

Representative examples of alkyl or arylamide groups for use herein include, by way of example, an amide of the general formula —$R^4C(O)NR^5R^6$ wherein $R^4$, $R^5$ and $R^6$ are independently $C_1$-$C_{30}$ hydrocarbons, e.g., $R^4$ can be alkylene groups, arylene groups, cycloalkylene groups and $R^5$ and $R^6$ can be alkyl groups, aryl groups, and cycloalkyl groups as defined herein and the like.

Representative examples of alkyl or arylamine groups for use herein include, by way of example, an amine of the general formula —$R^7NR^8R^9$ wherein $R^7$ is a $C_2$-$C_{30}$ alkylene, arylene, or cycloalkylene and $R^8$ and $R^9$ are independently $C_1$-$C_{30}$ hydrocarbons such as, for example, alkyl groups, aryl groups, or cycloalkyl groups as defined herein.

Representative examples of heterocyclic ring groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or Spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroquinolinyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, iso-oxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined herein. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined herein directly bonded to an alkyl group as defined herein. The heteroarylalkyl radical may be attached to the main structure at any carbon atom from the alkyl group that results in the creation of a stable structure.

Representative examples of heterocyclic groups for use herein include, by way of example, a substituted or unsubstituted heterocyclic ring radical as defined herein. The heterocyclic ring radical may be attached to the main structure at any heteroatom or carbon atom that results in the creation of a stable structure.

Representative examples of heterocycloalkyl groups for use herein include, by way of example, a substituted or unsubstituted heterocyclic ring radical as defined herein directly bonded to an alkyl group as defined herein. The heterocycloalkyl radical may be attached to the main structure at any carbon atom in the alkyl group that results in the creation of a stable structure.

The substituents in the 'substituted oxygen', 'substituted nitrogen', 'substituted sulfur', 'substituted alkyl', 'substituted alkylene', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' may be the same or different and include one or more substituents such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, and the like.

Another class of RAFT agents that can be used herein is of the general formula:

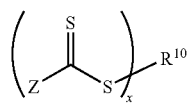

wherein x and Z have the aforestated meanings and $R^{10}$ is a substituted or unsubstituted carboxylic acid-containing group.

Representative examples of a carboxylic acid-containing group for use herein include, by way of example, a carboxylic acid group attached to the rest of the molecule via a linking group, e.g., of the general formula —$R^{11}$C(O)OH, wherein $R^{11}$ is a bond, a substituted or unsubstituted alkylene group, a substituted or unsubstituted cycloalkylene, a substituted or unsubstituted cycloalkylalkylene group, a substituted or unsubstituted arylene or a substituted or unsubstituted arylalkylene group as defined herein, e.g., —CH(Ar)(C(O)OH), —C(CH$_3$)(C(O)OH), and the like.

Representative examples of RAFT agents for use herein include, but are not limited to, benzyl dodecyl trithiocarbonate, ethyl-2-dodecyl trithiocarbonyl) proprionate, S-sec propionic acid O-ethyl xanthate, α-ethyl xanthylphenylacetic acid, ethyl α-(o-ethyl xanthyl) proprionate, ethyl α-(ethyl xanthyl)phenyl acetate, ethyl 2-(dodecyl trithiocarbonyl) phenyl acetate, ethyl 2-(dodecyl trithiocarbonyl) propionate, 2-(dodecylthiocarbonylthiol)propanoic acid, and the like and mixtures thereof.

There is no particular limitation on the organic chemistry used to form the RAFT agent and is within the purview of one skilled in the art. Also, the working examples below provide guidance. For example, the RAFT agents can be prepared as exemplified in Schemes I-III below.

SCHEME I

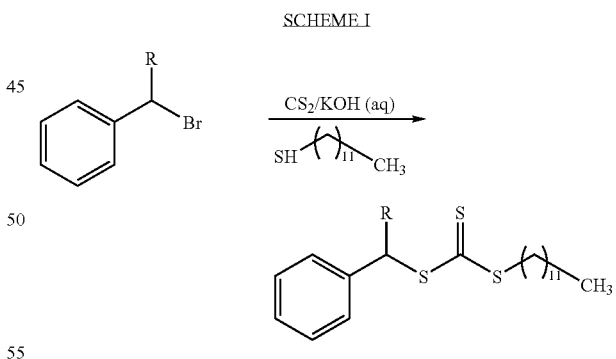

R = H, or Me

SCHEME II

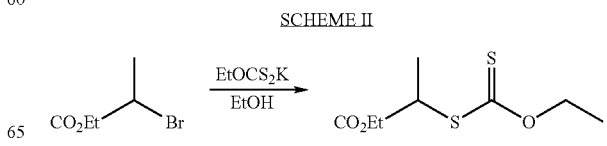

SCHEME III

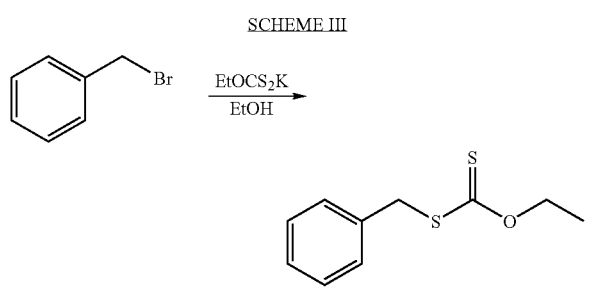

In addition to the one or more thio carbonyl thio fragments of a RAFT agent, the random copolymers described herein also contain one or more hydrophilic units and one or more hydrophobic units. In general, the hydrophilic unit(s) is derived from at least one ethylenically unsaturated polymerizable hydrophilic monomer. The term "ethylenically unsaturated polymerizable" as used herein shall be understood to include, by way of example, (meth)acrylate-containing radicals, (meth)acrylamide-containing radicals, vinyl-containing radicals such as vinyl radicals, vinyl carbonate-containing radicals, vinyl carbamate-containing radicals and the like, styrene-containing radicals, itaconate-containing radicals, vinyloxy-containing radicals, fumarate-containing radicals, maleimide-containing radicals, vinyl sulfonyl radicals and the like.

Suitable ethylenically unsaturated polymerizable hydrophilic monomers include, by way of example, acrylamides such as N,N-dimethylacrylamide, N,N-dimethylmethacrylamide, and the like; acetamides such as N-vinyl-N-methyl acetamide, N-vinyl acetamide and the like; formamides such as N-vinyl-N-methyl formamide, N-vinyl formamide, and the like; cyclic lactams such as N-vinyl-2-pyrrolidone and the like; (meth)acrylated alcohols such as 2-hydroxyethyl methacrylate, 2-hydroxyethyl acrylate and the like; (meth)acrylated poly(ethyleneglycol)s and the like; ethylenically unsaturated carboxylic acids such as methacrylic acid, acrylic acid and the like and mixtures thereof.

In one embodiment, the random copolymer containing one or more thio carbonyl thio fragments of a RAFT agent can also include a hydrophilic unit derived from an ethylenically unsaturated polymerizable monomer having ring-opening reactive functionalities. Such monomers may include one or more ring-opening reactive groups such as, for example, azlactone, epoxy, acid anhydrides, and the like. Suitable polymerizable monomers having ring-opening reactive functionalities include, but are not limited to, glycidyl methacrylate (GMA), maleic anhydride, itaconic anhydride and the like and mixtures thereof. The units derived from an ethylenically unsaturated polymerizable monomer having ring-opening reactive functionalities can be copolymerized with a hydrophilic comonomer to form hydrophilic units in the resulting random copolymer. Non-limiting examples of comonomers useful to be copolymerized with the ring-opening reactive functionalities of the monomer to form random copolymers used to prepare a biomedical device include those mentioned above, with dimethylacrylamide, hydroxyethyl methacrylate (HEMA), and/or N-vinylpyrrolidone being preferred. Alternatively, the unit derived from the ethylenically unsaturated polymerizable hydrophilic monomers having ring-opening reactive functionalities can be subjected to a ring-opening reaction, e.g., by hydrolyzing with water, and form hydrophilic units in the resulting random copolymer.

In another embodiment, the resulting random copolymers described herein contain units derived from ethylenically unsaturated polymerizable monomers have reactive functionalities which can be used to covalently attach other polymers having complementary reactive functionalities. Examples of such complementary reactive functionalities are described in U.S. Pat. Nos. 6,440,571 and 6,902,812.

In another embodiment, a hydrophilic unit can be derived from an ethylenically unsaturated polymerizable alkoxylated polymer. Suitable ethylenically unsaturated polymerizable alkoxylated polymers include, by way of example, polymerizable polyethylene glycols having a molecular weight of up to, for example, about 1000 such as those with CTFA names PEG-200, PEG-400, PEG-600, PEG-1000, and mixtures thereof. Representative examples include PEG-200 methacrylate, PEG-400 methacrylate, PEG-600 methacrylate, PEG-1000 methacrylate and the like and mixtures thereof.

In another embodiment, the random copolymers can also include a unit derived from a protected monomer such as, for example, nitrogen protected monomers, acetate protected monomers, e.g., vinyl acetate, and the like. In general, nitrogen protected monomers ("NPM") have an amino group that is protected by a nitrogen protecting group. As used herein, the term "nitrogen protecting group" means a group attached to a nitrogen atom to preclude that nitrogen atom from participating in a polymerization reaction. Although secondary amine groups can be protected in accordance with the invention, in most embodiments the protected amino group provides a primary amine group following deprotection.

Suitable nitrogen protecting groups include, but are not limited to: (a) "carbamate-type" groups of the formula C(O)O—R', wherein R' is an aromatic or aliphatic hydrocarbon group, which may be optionally substituted and which, taken together with the nitrogen atom to which it is attached forms a carbamate group; (b) "amide-type" groups of the formula —C(O)—R'' wherein R'' is for example methyl, phenyl, trifluoromethyl, and the like, which taken together with the nitrogen atom to which they are attached form an amide group; (c) "N-sulfonyl" derivatives, that is groups of the formula —$SO_2$—R''' wherein R''' is, for example, tolyl, phenyl, trifluoromethyl, 2,2,5,7,8-pentamethylchroman-6-yl-, 2,3,6-trimethyl-4-methoxybenzene, and the like.

Representative examples of nitrogen protecting groups include, but are not limited to, benzyloxycarbonyl (CBZ), p-methoxybenzyloxycarbonyl, p-nitrobenzyloxycarbonyl, tert-butoxycarbonyl (t-BOC), 9-flourenylmethyloxycarbonyl (Fmoc), 2-chlorobenzyloxycarbonyl, allyloxycarbonyl (alloc), 2-(4-biphenylyl)propyl-2-oxycarbonyl (Bpoc), 1-adamantyloxycarbonyl, trifluoroacetyl, toluene sulphonyl and the like.

In one embodiment, representative examples of t-Boc protected monomers include 2-(2-(tert-butoxycarbonylamino)acetoxy)ethyl methacrylate, 2-(2-(tert-butoxycarbonylamino)acetamido)ethyl methacrylate, 2-(tert-butoxycarbonylamino)ethyl methacrylate, tert-butyl 2-(vinyloxycarbonyloxy)ethylcarbamate, 2-(tert-butoxycarbonylamino)ethyl-N-vinylcarbamate, 3-(2-(tert-butoxycarbonylamino)acetoxy)-2-hydroxypropyl, N-(tert-Butoxycarbonyl)-L-glutamic acid methacryloxyethyl ester, 2-(tert-butoxycarbonylamino)-6-(3-(2-(methacryloyloxy)ethyl)ureido)hexanoic acid, 2-(tert-butoxycarbonylamino)-3-(methacryloyloxy)propanoic acid, 2-(tert-butoxycarbonylamino)-6-methacrylamidohexanoic acid and the like.

The nitrogen protecting groups present in the random copolymer can be readily removed post-polymerization by well known methods in the chemical art, e.g., to provide a hydrophilic unit in the random copolymer. Techniques for protecting amino nitrogen atoms with nitrogen protecting groups, and for deprotecting amino nitrogen atoms after a particular reaction are well known in the chemical art. See, for example, Greene et al., Protective Groups in Organic Synthesis, John Wiley & Sons, 1991, and U.S. Provisional Ser. Nos. 61/113,736; 61/113,739; 61/113,742; and 61/113,746, the contents of which are incorporated by reference herein. By way of example, an NPM can be prepared by reaction of a nitrogen-protected amino acid or amino alcohol with an ethylenically unsaturated compound having a group reactive with the respective acid or an alcohol group. In some embodiments a nitrogen protected amino acid may also have an unprotected amine group or a hydroxyl group, and the second amine group or the hydroxyl group, respectively, is the site of reaction to attach the ethylenic unsaturation. If the nitrogen protected amino acid has multiple available sites of attachment of an ethylenically unsaturated group NPM monomers having two or more ethylenically unsaturated groups may be produced.

As one skilled in the art will readily understand, the protected monomers are usually hydrophobic in the "protected" or "blocked" form. In order to become more polar and hydrophilic, the protecting group (e.g., in the case of the t-Boc monomers) will need to be removed from the unit. This will result in the biomedical device becoming more hydrophilic in nature and the material could therefore retain more water. Methods for removing the protecting group are within the purview of one skilled in the art.

In addition to the one or more thio carbonyl fragments of a RAFT agent and one or more hydrophilic units, the random copolymers described herein also contain one or more hydrophobic units. In general, the hydrophobic units are derived from an ethylenically unsaturated polymerizable hydrophobic monomer. The term "ethylenically unsaturated polymerizable" as used herein shall be understood to include any of the ethylenically unsaturated moieties discussed herein above.

In one embodiment, a hydrophobic unit can be derived from an ethylenically unsaturated polymerizable fluorine-containing monomer. The ethylenically unsaturated-containing polymerizable radicals can be attached to the fluorine-containing monomer as pendent groups, terminal groups or both. Suitable polymerizable fluorine-containing monomers include fluorine substituted hydrocarbons having one or more polymerizable ethylenically unsaturated-containing radicals attached thereto and optionally containing one or more ether linkages, e.g., fluorine substituted straight or branched $C_1$-$C_{18}$ alkyl groups having one or more polymerizable ethylenically unsaturated-containing radicals attached thereto which may include ether linkages therebetween; fluorine substituted $C_3$-$C_{24}$ cycloalkyl groups having one or more polymerizable ethylenically unsaturated-containing radicals attached thereto which may include ether linkages therebetween; fluorine substituted $C_5$-$C_{30}$ aryl groups having one or more polymerizable ethylenically unsaturated-containing radicals attached thereto which may include ether linkages therebetween and the like.

Representative examples of polymerizable fluorine-containing monomers include, but are not limited to, 2,2,2-trifluoroethyl(meth)acrylate, 2,2,3,3-tetrafluoropropyl (meth)acrylate, 2,2,3,3,3-pentafluoropropyl(meth)acrylate, 1-trifluoromethyl-2,2,2-trifluoroethyl(meth)acrylate, 1H,1H,5H-octafluoropentyl(meth)acrylate, octafluoropentyl methacrylate, octafluoropentyl vinyl carbonate, octafluoropentyl n-vinyl carbamate, hexafluoroisopropyl(meth)acrylate, 2,2,3,3,4,4-hexafluorobutyl(meth)acrylate, pentafluorophenyl (meth)acrylate, pentafluorohexyl(meth)acrylate and the like and mixtures thereof.

In another embodiment, a hydrophobic unit can be derived from an ethylenically unsaturated polymerizable ester-containing monomer. Suitable ethylenically unsaturated polymerizable ester-containing monomers include, by way of example, polymerizable fatty acid ester-containing monomers include vinyl esters made from fatty acids having from 4 to about 26 carbon atoms, and preferably from about 12 to about 16 carbon atoms in the chain. Examples of suitable polymerizable fatty acid ester-containing monomers include, but are not limited to, vinyl laurate, vinyl nononoate, vinyl pivalate, vinyl crotanate, allyl crotanate, vinyl stearate and the like and mixtures thereof.

In another embodiment, a hydrophobic unit can be derived from an ethylenically unsaturated polymerizable polysiloxanylalkyl-containing monomer. Suitable polymerizable polysiloxanylalkyl-containing monomers include, but are not limited to, methacryloxypropyl tris(trimethylsiloxy)silane, 3-(trimethylsilyl)propyl vinyl carbonate; 3-(vinyloxycarbonylthio)propyl-[tris(trimethylsiloxy)silane]; 3-[tris(tri-methylsiloxy)silyl]propyl vinyl carbamate; 3-[tris(trimethylsiloxy)silyl]propyl allyl carbamate; 3-[tris(trimethylsiloxy) silyl]propyl vinyl carbonate, tris(trimethylsiloxy)silylpropyl methacrylamide and the like and mixtures thereof. In one embodiment, the polymerizable polysiloxanylalkyl-containing monomer is M1-MCR-C12 as shown in the formula below:

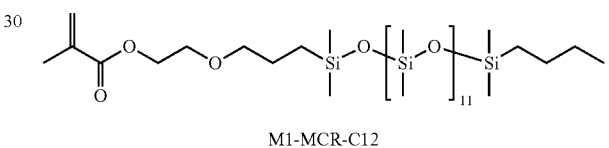

M1-MCR-C12

In one embodiment, a hydrophobic unit can be derived from an ethylenically unsaturated polymerizable monomer having ring-opening reactive functionalities. Such monomers may include one or more ring-opening reactive groups such as, for example, azlactone, epoxy, acid anhydrides, and the like. Suitable ethylenically unsaturated polymerizable monomers having ring-opening reactive functionalities include, but are not limited to, glycidyl methacrylate, glycidyl acrylate, glycidyl vinylcarbonate, glycidyl vinylcarbamate, 4,4-dimethyl-2-vinyloxazol-5(4H)-one, vinylcyclohexyl-1,2-epoxide, maleic anhydride, itaconic anhydride and the like and mixtures thereof.

In another embodiment, a hydrophobic unit can be derived from a hydrophobic monomer selected from the group consisting of alkyl(meth)acrylates, N-alkyl (meth)acrylamides, alkyl vinylcarbonates, alkyl vinylcarbamates, fluoroalkyl (meth)acrylates, N-fluoroalkyl(meth)acrylamides, N-fluoroalkyl vinylcarbonates, N-fluoroalkyl vinylcarbamates, silicone-containing (meth)acrylates, (meth)acrylamides, vinyl carbonates, vinyl carbamates, vinyl esters, styrenic monomers, polyoxypropylene (meth)acrylates and the like and combinations thereof. Representative examples of such hydrophobic monomers include methyl(meth)acrylate, ethyl (meth)acrylate, propyl(meth)acrylate, i-propyl (meth)acrylate, n-butyl(meth)acrylate, t-butyl(meth)acrylate, n-hexyl (meth)acrylate, cyclohexyl(meth)acrylate, octyl(meth) acrylate, decyl(meth)acrylate, undecyl(meth)acrylate, dodecyl methacrylate and lauryl(meth)acrylate, octafluoropentyl methacrylate, perfluorooctyl methacrylate, styrene, alpha-methyl styrene, ρ-methyl styrene, ρ-t-butyl monochloro styrene, and ρ-t-butyl dichloro styrene, methacryloyl oxypropyl tris(trimethylsiloxy)silane (TRIS), vinyl acetate, t-butyl allyl carbamate and mixtures thereof.

As disclosed in Example 12, the random copolymers can be obtained by (1) mixing the hydrophilic monomer, hydrophobic monomer and RAFT agent; (2) adding a polymerization initiator; (3) and subjecting the monomer/initiator mixture to a source of heat. Typical initiators include free-radical-generating polymerization initiators of the type illustrated by acetyl peroxide, lauroyl peroxide, decanoyl peroxide, coprylyl peroxide, benzoyl peroxide, tertiary butyl peroxypivalate, sodium percarbonate, tertiary butyl peroctoate, and azobisisobutyronitrile (AIBN). The level of initiator employed will vary within the range of 0.01 to 2 weight percent of the mixture of monomers. If desired, the mixture of the above-mentioned monomers is warmed with addition of a free-radical former.

The reaction can be carried out at a temperature of between about 15° C. to about 120° C. for a time period of about 30 minutes to about 48 hours. If desired, the reaction can be carried out in the presence of a suitable solvent. Suitable solvents are in principle all solvents which dissolve the monomer used, for example, 1,4-dioxane, hexanol, dimethylformamide; acetone, cyclohexanone, toluene, and the like and mixtures thereof.

As one skilled in the art will readily appreciate, the random copolymer will contain a balance of hydrophilic units and hydrophobic units in order to provide a suitable biomedical device. In general, the optimum balance of hydrophilic to hydrophobic units will be dependant on the desired properties and function of the biomedical device. Copolymers in the range of 5 to 50 mole percent hydrophobic component are generally considered most useful. The number of hydrophilic units in the random copolymer can vary widely, e.g., the number of hydrophilic units can range from 10 to about 3000, and preferably from about 50 to about 1800. The number of hydrophobic units in the random copolymer can vary widely, e.g., the number of units can range from 1 to about 405, and preferably from about 10 to about 200.

The resulting random copolymers will have a number average molecular weight ranging from about 1,000 to about 300,000 and about 10,000 to about 100,000.

The mixtures to be polymerized to form a biomedical device of the present invention can further include conventional biomedical device-forming or ophthalmic lens-forming monomers. As used herein, the term "monomer" or "monomeric" and like terms denote relatively low molecular weight compounds that are polymerizable by free radical polymerization, as well as higher molecular weight compounds also referred to as "prepolymers", "macromonomers", and related terms. Generally, the biomedical device-forming comonomer contains at least one polymerizable group or free radical polymerizable group. Suitable polymerizable groups or free radical polymerizable groups are selected from (meth)acrylate, (meth)acrylamide, styrenyl, alkenyl, vinyl carbonate, vinyl carbamate groups and mixtures thereof. In one embodiment, a suitable comonomer includes hydrophobic monomers, hydrophilic monomers and the like and mixtures thereof.

Representative examples of hydrophilic comonomers include, but are not limited to, unsaturated carboxylic acids, such as methacrylic and acrylic acids; (meth)acrylic substituted alcohols or polyols such as 2-hydroxyethyl methacrylate, 2-hydroxyethyl acrylate, glyceryl methacrylate and the like; vinyl lactams such as N-vinylpyrrolidone; and (meth)acrylamides such as methacrylamide, N,N-dimethylacrylamide and the like and combinations thereof. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the mixtures in an amount ranging from about 0.1 to about 90 weight percent, based on the total weight of the mixture.

According to various preferred embodiments, the initial mixture to be polymerized can comprise at least one (meth)acrylic substituted alcohol, such as at least one of 2-hydroxyethyl methacrylate and glyceryl methacrylate, preferably in an amount of at least about 0.1 to about 50 weight percent. Preferably, the mixture to be polymerized further includes at least one vinyl lactam, such as N-vinylpyrrolidone and/or at least one (meth)acrylamide, such as N,N-dimethylacrylamide.

Suitable hydrophobic monomers include $C_1$-$C_{20}$ alkyl and $C_3$-$C_{20}$ cycloalkyl (meth)acrylates, substituted and unsubstituted $C_6$-$C_{30}$ aryl(meth)acrylates, (meth)acrylonitriles, fluorinated alkyl methacrylates, long-chain acrylamides such as octyl acrylamide, and the like. The hydrophobic monomers can be present in the mixtures in an amount ranging from about 0.1 to about 90 weight percent, based on the total weight of the mixture.

Another class of biomedical device-forming or lens-forming monomers is silicone-containing monomers. In other words, a silicone-containing comonomer which contains from 1 to about 60 silicone atoms, in addition to the random copolymer, may be included in the initial mixture, for example, if it is desired to obtain a polymerization product with high oxygen permeability. Applicable silicone-containing monomers for use in the formation of contact lenses such as silicone hydrogels are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth)acrylic monomer is represented by the structure of Formula I:

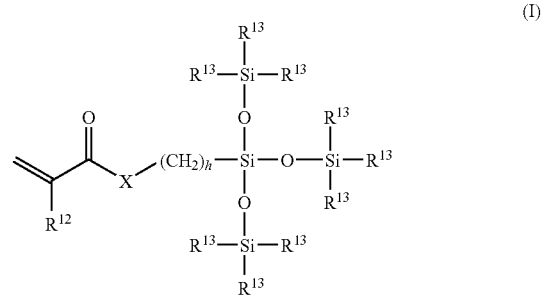

(I)

wherein X denotes —O— or —NR— wherein R denotes hydrogen or a $C_1$-$C_4$ alkyl; $R^{12}$ independently denotes hydrogen or methyl; each $R^{13}$ independently denotes a lower alkyl radical, phenyl radical or a group represented by

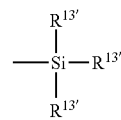

wherein each $R^{13'}$ independently denotes a lower alkyl or phenyl radical; and h is 1 to 10.

Representative examples of other applicable silicon-containing monomers includes, but are not limited to, bulky polysiloxanylalkyl carbamate monomers as generally depicted in Formula Ia:

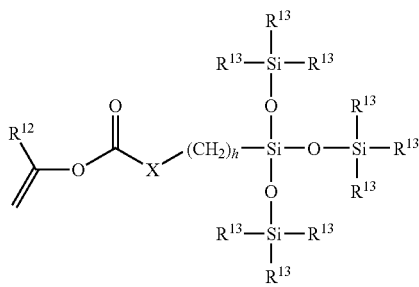

(Ia)

wherein X denotes —NR—; wherein R denotes hydrogen or a $C_1$-$C_4$ alkyl; $R^{12}$ denotes hydrogen or methyl; each $R^{13}$ independently denotes a lower alkyl radical, phenyl radical or a group represented by

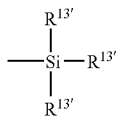

wherein each $R^{13'}$ independently denotes a lower alkyl or phenyl radical; and h is 1 to 10, and the like.

Examples of bulky monomers are 3-methacryloyloxypropyltris(trimethylsiloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyldisiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacrylates in Polyurethane-Polysiloxane Hydrogels," Journal of Applied Polymer Science, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae II and III:

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A denotes a divalent polymeric radical of Formula IV:

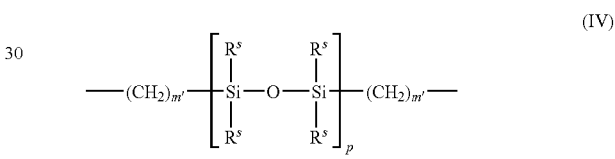

(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

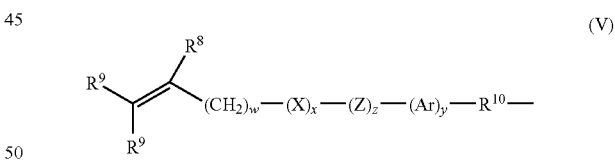

(V)

wherein: $R^8$ is hydrogen or methyl;

$R^9$ is independently hydrogen, an alkyl radical having 1 to 6 carbon atoms, or a —CO—Y—$R^{11}$ radical wherein Y is —O—, —S— or —NH—;

$R^{10}$ is a divalent alkylene radical having 1 to about 10 carbon atoms;

$R^{11}$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

A preferred silicone-containing urethane monomer is represented by Formula VI:

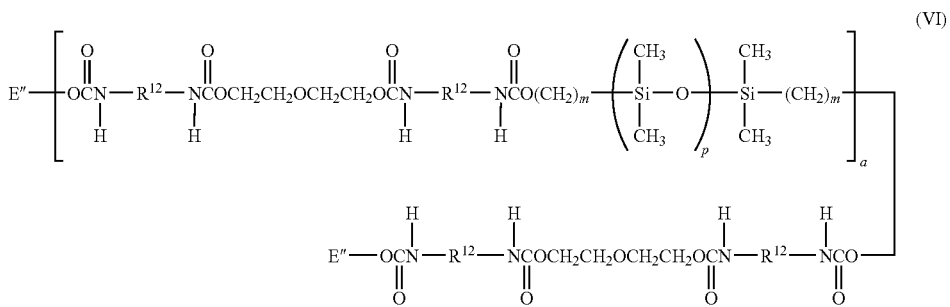

(VI)

wherein m is at least 1 and is preferably 3 or 4, a is at least 1 and preferably is 1, p is a number which provides a moiety weight of about 400 to about 10,000 and is preferably at least about 30, $R^{12}$ is a diradical of a diisocyanate after removal of the isocyanate group, such as the diradical of isophorone diisocyanate, and each E" is a group represented by:

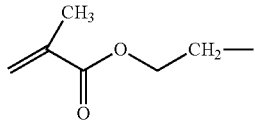

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954,587; 5,010,141 and 5,079,319. The use of silicone-containing monomers having certain fluorinated side groups, i.e., —($CF_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming biomedical devices according to the present invention and have been disclosed in various publications and are being continuously developed for use in contact lenses and other biomedical devices can also be used. For example, a biomedical device-forming comonomer can be a cationic monomer such as cationic silicone-containing monomer or cationic fluorinated silicone-containing monomers.

The mixtures to be polymerized may include the silicone comonomer, in addition to the subject random copolymer, at 0 to about 50 weight percent, preferably about 5 to about 30 weight percent when present.

The mixtures to be polymerized can also include a crosslinking monomer (a crosslinking monomer being defined as a monomer having multiple polymerizable functionalities). Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a crosslinking agent is employed, this monomeric material may be included in the monomer mixture at about 0.1 to about 20 weight percent, and more preferably at about 0.2 to about 10 weight percent.

Although not necessarily required, copolymers within the scope of the present invention may optionally have one or more strengthening agents added prior to polymerization, preferably in quantities of less than about 80 weight percent and preferably from about 20 to about 60 weight percent. Non-limiting examples of suitable strengthening agents are described in U.S. Pat. Nos. 4,327,203; 4,355,147; and 5,270,418; each of which is incorporated herein in its entirety by reference. Specific examples, not intended to be limiting, of such strengthening agents include cycloalkyl acrylates and methacrylates; e.g., tert-butylcyclohexyl methacrylate and isopropylcyclopentyl acrylate.

The mixtures to be polymerized may further contain, as necessary and within limits not to impair the purpose and effect of the present invention, various additives such as an antioxidant, coloring agent, ultraviolet absorber, lubricant internal wetting agents, toughening agents and the like and other constituents as is well known in the art.

The biomedical devices of the present invention, e.g., contact lenses or intraocular lenses, can be prepared by polymerizing the foregoing mixtures to form a product that can be subsequently formed into the appropriate shape by, for example, lathing, injection molding, compression molding, cutting and the like. For example, in producing contact lenses, the initial mixture may be polymerized in tubes to provide rod-shaped articles, which are then cut into buttons. The buttons may then be lathed into contact lenses.

Alternately, the biomedical devices such as contact lenses may be cast directly in molds, e.g., polypropylene molds, from the mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the mixtures to be polymerized to a mold, and spinning the mold in a controlled manner while exposing the mixture to a radiation source such as UV light. Static casting methods involve charging the mixture between two mold sections, one mold section shaped to form the anterior lens surface and the other mold section shaped to form the posterior lens surface, and curing the mixture while retained in the mold assembly to form a lens, for example, by free radical polymerization of the mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarybutyl peroxypivalate, peroxydicarbonate, and the like. Representative UV initiators are those known in the art and include benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the mixture at a concentration of about 0.01 to about 5 percent by weight of the total mixture.

Polymerization is generally performed in a reaction medium, such as, for example, a solution or dispersion using a solvent, e.g., water or an alkanol containing from 1 to 12 carbon atoms such as methanol, ethanol or propan-2-ol. Alternatively, a mixture of any of the above solvents may be used.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

Polymerization of the mixtures will yield a polymer, that when hydrated, preferably forms a hydrogel. Generally, the mixture will contain the random copolymer comprising one or more hydrophilic units, one or more hydrophobic units and one or more thio carbonyl thio fragments of a RAFT agent in an amount ranging from about 0.25 to about 50 weight percent, and preferably about 2.5 to about 10 weight percent, based on the total weight of the mixture. The biomedical device-forming comonomer may be present in the mixture in an amount ranging from about 85 to about 99.75 weight percent, and preferably from about 90.5 to about 97.5 weight percent, based on the total weight of the mixture.

When producing a hydrogel lens, the mixture may further include at least a diluent that is ultimately replaced with water when the polymerization product is hydrated to form a hydrogel. Generally, the water content of the hydrogel is greater than about 5 weight percent and more commonly between about 10 to about 80 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

In the case of intraocular lenses, the mixtures to be polymerized may further include a monomer for increasing the refractive index of the resultant copolymer. Examples of such monomers are aromatic (meth)acrylates, such as phenyl (meth)acrylate, 2-phenylethyl(meth)acrylate, 2-phenoxyethyl methacrylate, and benzyl(meth)acrylate.

The biomedical devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

In the examples, the following abbreviations are used.

DMA: N,N-dimethylacrylamide

HEMA: 2-hydroxyethyl methacrylate

NVP: N-vinyl-2-pyrrolidone

AIBN: azo bis-isobutylnitrile (Vazo™ 64)

TRIS: 3-methacryloxypropyltris(trimethylsiloxy)silane

HEMAVC: methacryloxyethyl vinyl carbonate

IMVT: 1,4-bis(4-(2-methacryloxyethyl)phenylamino)anthraquinone

N-V t-BocEA: 2-(tert-butoxycarbonylamino)ethyl-N-vinylcarbamate having the structure:

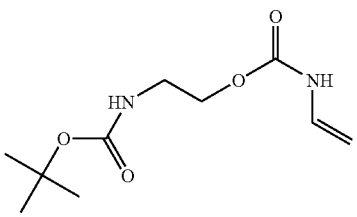

Allyl carbamate t-boc: Tert-butyl allylcarbamate having the structure:

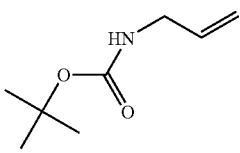

VDMO: 4,4-dimethyl-2-vinyloxazol-5(4H)-one

Example 1

Preparation of Ethyl α-(o-Ethyl Xanthyl) Proprionate Having the Following Structure

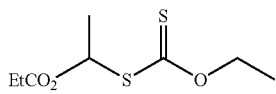

A 500 mL round bottom 3 neck flask was fitted with a magnetic stirrer, nitrogen inlet, and a temperature probe. Ethyl-2-bromo propionate (27.2 g) and 500 mL absolute ethanol were combined and stirred for 20 minutes under nitrogen. The reaction flask was placed in an ice/water bath at 0° C. Potassium O-ethyl xanthate (26.4 g) was slowly added using a powder funnel. The funnel was rinsed with an additional 50 mL of ethanol. The reaction flask was allowed to stir for an additional 24 hours at room temperature. Deionized water (250 mL) was then added to the reaction flask. The crude mixture was extracted 4 times with 200 mL of 2:1 hexane:ethyl ether retaining the organic layers. The combined organic layers were dried over sodium sulfate, filtered and solvent was removed under reduced pressure to obtain 32.22 grams of the desired product (a 97% yield).

Example 2

Preparation of α-(Ethyl Xanthyl) Toluene Having the Following Structure

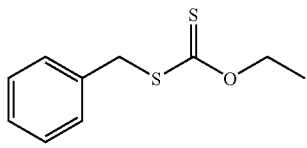

A 250 mL round bottom 3 neck flask was fitted with a magnetic stirrer, nitrogen inlet, Freidrich's condenser, and a temperature probe. After absolute ethanol (125 mL), and benzyl bromide (14.4 g) were added, the reaction flask was placed in an ice/water bath at 0° C. and stirred for 1 hour. Potassium O-ethyl xanthate (17.63 g) was added slowly to the reaction flask using a powder funnel. The reaction flask was stirred for an additional 16 hours at room temperature and 200 mL of purified water was added to the flask. The crude mixture was extracted 3 times with 200 mL of 2:1 pentane:ethyl ether retaining the organic layers. The combined organic layers were dried over anhydrous sodium sulfate, filtered and solvent was removed under reduced pressure leaving 15.09 grams (an 84.6% yield) of the desired product.

Example 3

Preparation of (1-Phenyl Ethyl) Ethyl Xanthate Having the Following Structure

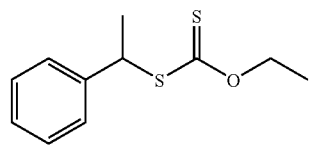

A 500 mL round bottom 3 neck flask was fitted with a magnetic stirrer, nitrogen inlet, and a temperature probe, 1-bromoethyl benzene (20.5 mL) and 200 mL absolute ethanol were added. The reaction flask was placed in an ice/water bath at 0° C. Potassium O-ethyl xanthate was added slowly using a powder funnel rinsed into the reaction flask with an additional 100 mL ethanol. The reaction flask was allowed to stir for an additional 24 hours at room temperature and then 250 mL of purified water was added. The crude mixture was extracted 4 times with 200 mL of 2:1 heptane:ethyl ether retaining the organic layers. The combined organic layers were dried over anhydrous sodium sulfate, filtered and the solvent was removed under reduced pressure to yield 31.42 grams of crude product. A portion, 15 grams, of the crude product was eluted from a silica gel column using hexane to give 12.81 grams of the pure product.

Example 4

Preparation of Naphthyl-O-Ethyl Xanthate Having the Following Structure

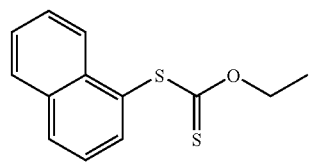

A 1000 mL round bottom 3 neck flask fitted with a mechanical stirrer, nitrogen inlet, Freidrich's condenser, and a temperature probe was charged with 500 mL of ethanol: 1,4 dioxane, and 2-(bromomethyl naphthalene) (22.1 g). The reaction flask was placed in an ice/water bath at 0° C. and potassium O-ethyl xanthate (17.63 g) was added slowly using a powder funnel. The reaction stirred for an additional 16 hours at room temperature and 500 mL of purified water was added. The crude mixture was extracted 2 times with 500 mL of 50:50 hexane:ethyl ether, hexane, and methylene chloride retaining the organic layers. The combined organic layers were dried over anhydrous sodium sulfate, filtered and solvent was removed under reduced pressure leaving the product, a yellow oil 22.52 g (an 85.8% yield).

Example 5

Preparation of S-Sec Propionic Acid O-Ethyl Xanthate

A 1000 mL round bottom 3 neck flask was equipped with a Friedrich condenser, a magnetic stirring bar, nitrogen inlet, and a temperature probe. 2-Bromo propionic acid and 600 mL absolute ethanol were combined and stirred for 20 minutes under nitrogen. Potassium O-ethyl xanthate was added slowly using a powder funnel to the reaction flask and rinsed with an additional 50 mL of ethanol. The reaction flask was allowed to stir at a gentle reflux over night and then quenched with 250 mL of DI water. The mixture was acidified with HCl and then extracted 3 times with 250 ml portions of ether. The combined organic layers were dried over magnesium sulfate and the solvents were removed from he filtrate by flash evaporation leaving 26.3 grams of crude product a light orange liquid. This reaction is generally shown below in Scheme IV.

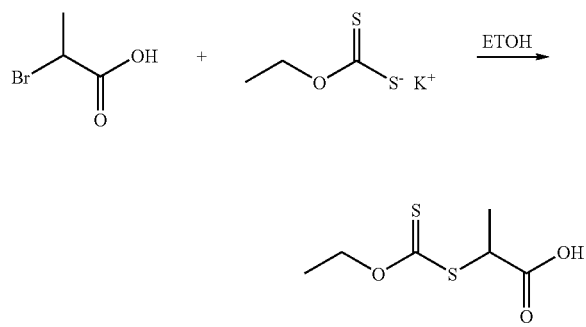

Example 6

Preparation of α-Ethyl Xanthylphenylacetic Acid

A 1000 mL round bottom 3 neck flask was fitted with a magnetic stirrer, nitrogen inlet, and a temperature probe, α-Bromophenylacetic acid (21.5 g) and 300 mL ethanol were added. Potassium O-ethyl xanthate was added slowly using a powder funnel rinsed into the reaction flask with an additional 100 mL absolute ethanol. The reaction flask was allowed to stir for an additional 24 hours at 60° C. and then 250 mL of purified water was added. The crude mixture was extracted 4 times with 200 mL of chloroform retaining the organic layers. The combined organic layers were dried over anhydrous sodium sulfate, filtered and the solvent was removed under reduced pressure to yield 5.18 grams the resulting product, a viscous liquid. This reaction is generally shown below in Scheme V.

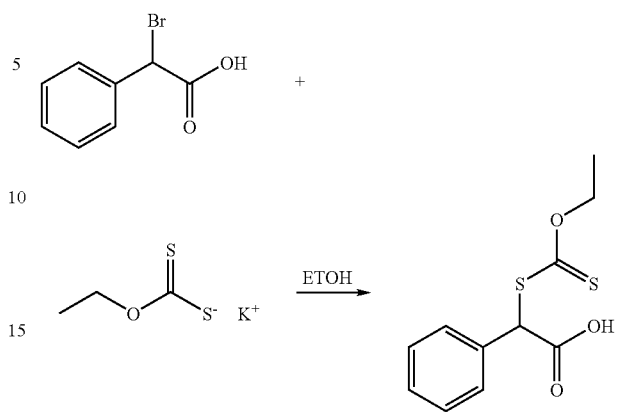

Example 7

Preparation of 2(Dodecylthiocarbonylthiol)Propanoic Acid

A reaction flask was fitted a magnetic stirrer, ice bath, dropping funnel and a nitrogen inlet. The flask was charged with ethyl ether (150 ml) and 60% sodium hydride (6.3 grams). With stirring, dodecylmercaptan (30.76 grams) was slowly added to the cold slurry (temperature 5-10° C.). The grayish slurry was converted to a thick white slurry (sodium thiodecylate) with vigorous evolution of $H_2$ gas. The mixture was cooled to 0° C. and carbon disulfide (12 g) was added. Following the addition, the ice bath was removed and the reaction was allowed to reach room temperature and the addition of 2-bromopropanoic acid (23.3 grams) followed by stirring overnight. The solution was filtered to remove the salt and recrystallization from heptane gave 21 grams of pale yellow needles. This reaction is generally shown below in Scheme VI.

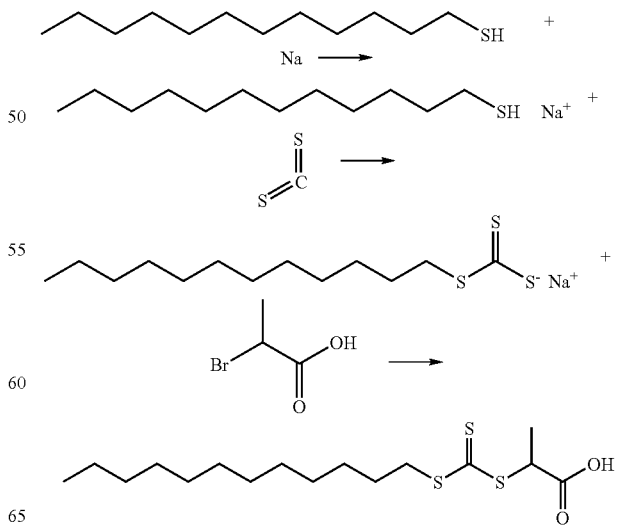

Example 8

Preparation of Ethyl α-(o-Ethyl Xanthyl) Proprionate

A 500 mL round bottom 3 neck flask was equipped with a Friedrich condenser, a magnetic stirring bar, nitrogen inlet, and a temperature probe. Ethyl-2-bromo propionate and 500 mL absolute ethanol were added and stirred for 20 minutes under nitrogen. The reaction flask was placed in an ice bath at 0°±3° C. Potassium O-ethyl xanthate was added slowly to the reaction flask using a powder funnel and rinsed with an additional 50 mL of ethanol. The reaction flask was allowed to stir and equilibrate to room temperature over a period of 24 hours. DI water (250 mL) was added to quench the reaction. The crude mixture was extracted 4 times with 200 mL of 2:1 hexane:ethyl ether retaining the organic layers. The combined organic layers were dried over sodium sulfate, filtered and solvent was removed under reduced pressure.

Example 9

Preparation of Ethyl α-(Ethyl Xanthyl) Phenyl Acetate

A 500 mL round bottom 3 neck flask was equipped with a magnetic stirrer, nitrogen inlet, Friedrich's condenser and a temperature probe. Ethyl (2-bromo-2-phenyl)acetate and 250 mL absolute ethanol were added and stirred for 20 minutes under nitrogen. The reaction flask was placed in an ice/water bath at 0° C. Potassium O-ethyl xanthate was added slowly using a powder funnel and rinsed into the reaction flask with an additional 50 mL of ethanol. The reaction flask was allowed to stir for an additional 24 hours at room temperature. DI water (250 mL) was then added to the reaction flask. The crude mixture was extracted 4 times with 200 mL of 2:1 hexane:ethyl ether retaining the organic layers. The combined organic layers were dried over sodium sulfate, filtered and solvent was removed under reduced pressure. Yield, 96%.

Example 10

Preparation of Ethyl 2-(Dodecyl Trithiocarbonyl) Proprionate

A 250 mL round bottom 3 neck flask was equipped with a mechanical stirrer, Friedrich's condenser and a temperature probe. Carbon disulfide and dodecanethiol were added to the flask with 65 mL chloroform. Triethylamine was added drop wise using an addition funnel with 10 mL chloroform. The reaction stirred for 3 hours at room temperature. Ethyl-α-bromo proprionate was added drop wise using an addition funnel with 25 mL chloroform. The reaction flask was allowed to stir for an additional 24 hrs at room temperature. The crude mixture was washed 2 times each with 250 mL of DI water, 5% HCl, and 5% Brine retaining the organic layers. The organic layers were dried over magnesium sulfate, filtered and solvent was removed under pressure. The product was further purified by column chromatography on silica gel using hexane:ethyl acetate.

Example 11

Preparation of Ethyl-α-(Dodecyl Trithiocarbonyl) Phenyl Acetate

A 250 mL round bottom 3 neck flask was equipped with a mechanical stirrer, Friedrich condenser and a temperature probe. Carbon disulfide and dodecanethiol were added to the flask with 65 mL chloroform. Triethylamine was added dropwise using an addition funnel with 10 mL chloroform. The reaction stirred for 3 hours at room temperature. Ethyl-α-bromophenyl acetate was added drop wise using an addition funnel with 35 mL chloroform. The reaction flask was allowed to stir for an additional 24 hours at room temperature. The crude mixture was washed 2 times with 250 mL of DI water, 5% HCl (aq), and 5% Brine retaining the organic layers. The organic layers were dried over magnesium sulfate, filtered and solvent was removed under pressure. The product was further purified by column chromatography on silica gel using hexane:ethyl acetate.

Example 12

Preparation of a Random Copolymer of N-Vinyl-2-Pyrrolidinone (NVP) and Octafluoropentylvinylcarbonate (80/20)

An oven dried round bottom reaction flask fitted with a septum, magnetic stirrer and a thermo controller. The flask was charged with NVP, (20.8 g) anhydrous 1,4-dioxane (50 ml), the RAFT agent of Example 1 (0.156 g, 7×10 moles), and octafluoropentylvinylcarbonate (14.14 g, 0.0468 moles). This reaction mixture was allowed to stir for a suitable period of time to provide a homogeneous solution. Next, AIBN ($1.52 \times 10^{-4}$ moles=0.025 g) was added to the homogeneous mixture. Dry nitrogen was bubbled through the reaction mixture for 30 minutes to remove dissolved oxygen. The vessel was then heated at 60° C. under a passive blanket of nitrogen overnight. The random copolymer was isolated by precipitation into a large volume (3 L) of ethyl ether. The isolated yield of the random copolymer was 31.08 grams (89%). The random copolymer was characterized as follows: $M_n$=90401 Daltons, $M_w$=131886 Daltons, $M_z$=154686 Daltons, $M_p$=168248 Daltons and a polydispersity of 1.46. This reaction is generally shown below in Scheme VII.

SCHEME VII

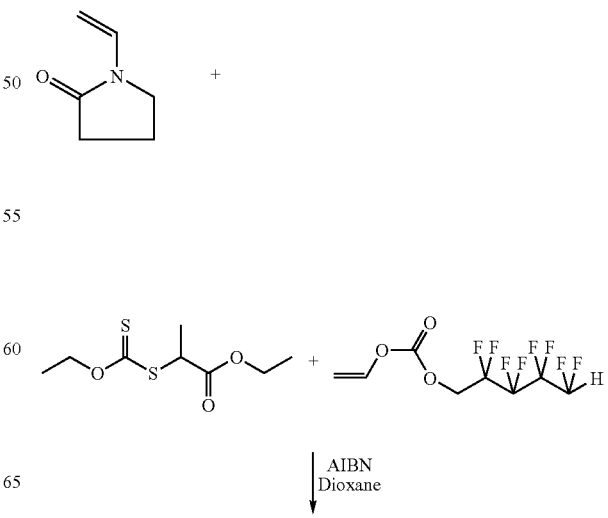

-continued

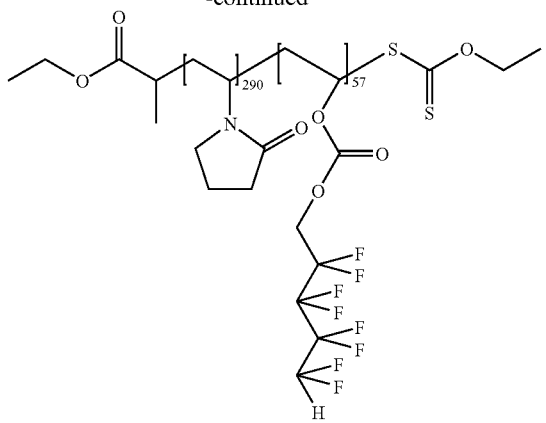

Examples 13-43

Preparation of Random Copolymers

The random copolymers of these examples were prepared in substantially the same manner as in Example 12 using the RAFT agent of Example 1. The reagents and amounts for each example are set forth below in Table 1.

The random copolymers of Examples 13-43 had the following characteristics as set forth below in Table 2.

TABLE 2

| Ex. | Mn, (calcd) | Mol. Weight Data | | | |
|---|---|---|---|---|---|
| | | Method | Mn | Mw | Polydisp. |
| 13 | 59,598 | — | — | — | — |
| 14 | 56,805 | — | — | — | — |
| 15 | 53,206 | — | — | — | — |
| 16 | 56,550 | — | — | — | — |
| 17 | 59,227 | SEC | 39,164 | 58,855 | 1.503 |
| 18 | 112,923 | — | — | — | — |
| 19 | 52,724 | SEC | 2,784 | 2,990 | 1.074 |
| 20 | 51,964 | — | — | — | — |
| 21 | 52,460 | SEC | 31,569 | 53,678 | 1.7 |
| 22 | 51,118 | SEC | 24,271 | 42,598 | 1.755 |
| 23 | 57,208 | SEC | 57,023 | 79,223 | 1.39 |
| 24 | 54,497 | SEC | 62,824 | 74,998 | 1.194 |
| 25 | 59,009 | SEC | 51,707 | 80,416 | 1.555 |
| 26 | 60,178 | SEC | 48,232 | 77,591 | 1.609 |
| 27 | 112,431 | — | — | — | — |
| 28 | 55,370 | — | — | — | — |
| 29 | 54,630 | SEC | 62,824 | 74,998 | 1.194 |
| 30 | 26,472 | — | — | — | — |
| 31 | 5,211 | — | — | — | — |
| 32 | 42,187 | — | — | — | — |
| 33 | 9,433 | — | — | — | — |
| 34 | 27,110 | — | — | — | — |

TABLE 1

| | Solvent | | Monomer | | Co-monomer | | RAFT Reagent | | Yield |
|---|---|---|---|---|---|---|---|---|---|
| Ex. | Solvent | Volume (mL) | Monomer 1 | (g) | Monomer 2 | (g) | Agent | (g) | — |
| 13 | 1,4 Dioxane | 20 | NVP | 20.8 | N-V t-BocEA | 2.16 | EX. 1 | 0.086 | 17.03 |
| 14 | 1,4 Dioxane | 20 | NVP | 20.8 | N-V t-BocEA | 1.08 | EX. 1 | 0.086 | 17.88 |
| 15 | 1,4 Dioxane | 20 | DMA | 18.6 | N-V t-BocEA | 2.16 | EX. 1 | 0.087 | Gelled |
| 16 | 1,4 Dioxane | 20 | NVP | 20.8 | N-V t-BocEA | 1.08 | EX. 1 | 0.086 | 19.42 |
| 17 | 1,4 Dioxane | 50 | NVP | 20.8 | N-V t-BocEA | 2.036 | EX. 1 | 0.086 | 9.76 |
| 18 | 1,4 Dioxane | 100 | NVP | 41.6 | N-V t-BocEA | 4.01 | EX. 1 | 0.090 | — |
| 19 | 1,4 Dioxane | 100 | NVP | 41.6 | N-V t-BocEA | 4.33 | EX. 1 | 0.176 | 45.40 |
| 20 | 1,4 Dioxane | 100 | NVP | 41.6 | Vinyl Acetate | 1.64 | EX. 1 | 0.179 | — |
| 21 | 1,4 Dioxane | 100 | NVP | 41.6 | Allyl carbamate t-boc | 2.95 | EX. 1 | 0.177 | |
| 22 | 1,4 Dioxane | 100 | NVP | 41.6 | Allyl carbamate t-boc | 5.95 | EX. 1 | 0.182 | |
| 23 | 1,4 Dioxane | 100 | NVP | 42.6 | Vinyl acetate | 1.61 | EX. 1 | 0.173 | 42.88 |
| 24 | 1,4 Dioxane | 100 | NVP | 41.6 | Vinyl Acetate | 1.72 | EX. 1 | 0.178 | — |
| 25 | 1,4 Dioxane | 100 | NVP | 41.6 | Vinyl Acetate | 3.64 | EX. 1 | 0.171 | — |
| 26 | 1,4 Dioxane | 100 | NVP | 41.6 | Vinyl Acetate | 5.77 | EX. 1 | 0.176 | — |
| 27 | 1,4 Dioxane | 100 | NVP | 20.8 | Octafluoro pentyl vinyl carbonate | 5.89 | EX. 1 | 0.053 | 22.34 |
| 28 | 1,4 Dioxane | 100 | DMA | 39.9 | Octafluoro pentyl methacrylate | 5.74 | EX. 1 | 0.184 | 32.66 |
| 29 | 1,4 Dioxane | 100 | NVP | 41.6 | Vinyl Acetate | 1.75 | EX. 1 | 0.177 | — |
| 30 | 1,4 Dioxane | 60 | NVP | 24.2 | Itaconic Anhydride | 1.25 | EX. 1 | 0.216 | — |
| 31 | 1,4 Dioxane | 60 | NVP | 23.9 | Itaconic Anhydride | 1.23 | EX. 1 | 1.121 | — |
| 32 | 1,4 Dioxane | 50 | NVP | 22.4 | Itaconic Anhydride | 1.25 | EX. 1 | 0.125 | — |
| 33 | 1,4 Dioxane | 50 | NVP | 21.8 | Itaconic Anhydride | 1.23 | EX. 1 | 0.557 | — |
| 34 | 1,4 Dioxane/Hexanol | 30/30 | NVP | 24.2 | Itaconic Anhydride | 1.26 | EX. 1 | 0.211 | — |
| 35 | 1,4 Dioxane/Hexanol | 25/25 | NVP | 22.4 | Itaconic Anhydride | 1.25 | EX. 1 | 0.126 | — |
| 36 | 1,4 Dioxane | 100 | NVP | 41.6 | Vinyl Acetate | 1.73 | EX. 1 | 0.173 | — |
| 37 | 1,4 Dioxane | 100 | NVP | 41.6 | Vinyl Acetate | 3.25 | EX. 1 | 0.179 | — |
| 38 | 1,4 Dioxane | 100 | NVP | 41.6 | Vinyl Acetate | 4.90 | EX. 1 | 0.174 | — |
| 39 | 1,4 Dioxane | 100 | NVP | 41.6 | Vinyl Acetate | 1.73 | EX. 1 | 0.179 | — |
| 40 | 1,4 Dioxane | 100 | NVP | 41.6 | Vinyl Acetate | 3.23 | EX. 1 | 0.178 | — |
| 41 | 1,4 Dioxane | 100 | NVP | 41.6 | Vinyl Acetate | 4.90 | EX. 1 | 0.174 | — |
| 42 | 1,4 Dioxane | 100 | NVP | 41.6 | VDMO | 7.96 | EX. 1 | 0.217 | — |
| 43 | 1,4 Dioxane | 100 | NVP | 41.6 | Maleic Anhydride | 4.07 | EX. 1 | 0.107 | — |

TABLE 2-continued

| Ex. | Mn, (calcd) | Method | Mn | Mw | Polydisp. |
|---|---|---|---|---|---|
| 35 | 42,025 | — | — | — | — |
| 36 | 56,052 | SEC | 24272 | 39000 | 1.6068 |
| 37 | 56,039 | SEC | 23865 | 40422 | 1.6938 |
| 38 | 59,665 | SEC | 23977 | 40888 | 1.7053 |
| 39 | 54,116 | SEC | — | — | — |
| 40 | 56,441 | SEC | — | — | — |
| 41 | 59,798 | SEC | — | — | — |
| 42 | 51,040 | SEC | 20750 | 22141 | 1.067 |
| 43 | 95,420 | SEC | 8562635 | 13833083 | 1.6155 |

Example 44

Preparation of a Contact Lens

A mixture is made by mixing the following components listed in Table 3, at amounts per weight.

TABLE 3

| Ingredient | Weight Percent |
|---|---|
| Polyurethane-siloxane prepolymer | 53 |
| TRIS | 15 |
| NVP | 33 |
| HEMA | 5 |
| HEMAVC | 1 |
| Random Copolymer of Example 12 | 1 |
| N-hexanol | 15 |
| Vazo-64 | 0.5 |
| IMVT | 150 ppm |

The resulting mixture is cast into contact lenses by introducing the mixture to a mold assembly composed of an ethyl vinyl alcohol mold for the anterior surface and an ethyl vinyl alcohol mold for the posterior surface and thermally curing the mixture at 100° C. for 2 hours. The resulting contact lens is released from the mold, extracted with isopropyl alcohol for 4 hours and placed in buffer solution.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biomedical device comprising a polymerization product of a mixture comprising a random copolymer comprising hydrophilic units and hydrophobic units, wherein the random copolymer has at least one thio carbonyl thio fragment of a reversible addition fragmentation chain transfer ("RAFT") agent.

2. The biomedical device of claim 1, wherein the thio carbonyl thio fragment comprises a dithioester group, xanthate group, dithiocarbamate group or trithiocarbonate group.

3. The biomedical device of claim 1, wherein the hydrophilic units are derived from a hydrophilic monomer selected from the group consisting of an unsaturated carboxylic acid, acrylamide, vinyl lactam, ethylenically unsaturated poly (alkylene oxide), (meth)acrylic acid, hydroxyl-containing-(meth)acrylate, hydrophilic vinyl carbonate, hydrophilic vinyl carbamate monomer, hydrophilic oxazolone monomer, and mixtures thereof.

4. The biomedical device of claim 1, wherein the hydrophilic units are derived from a hydrophilic monomer selected from the group consisting of methacrylic acid, acrylic acid, 2-hydroxyethylmethacrylate, 2-hydroxyethylacrylate, N-vinyl pyrrolidone, methacrylamide, N,N-dimethylacrylamide, ethylene glycol dimethacrylate and mixtures thereof.

5. The biomedical device of claim 1, wherein the hydrophilic units are derived from an ethylenically unsaturated polymerizable alkoxylated polymer selected from the group consisting of polyethylene glycol (PEG)-200 methacrylate, PEG-400 methacrylate, PEG-600 methacrylate, PEG-1000 methacrylate and mixtures thereof.

6. The biomedical device of claim 1, wherein the random copolymer has a number average molecular weight of about 1000 to about 300,000.

7. The biomedical device of claim 1, wherein the random copolymer has a number average molecular weight of about 10,000 to about 100,000.

8. The biomedical device of claim 1, wherein the hydrophobic units are derived from a hydrophobic monomer selected from the groups consisting of an ethylenically unsaturated polymerizable fluorine-containing monomer, ethylenically unsaturated polymerizable fatty acid ester-containing monomer, ethylenically unsaturated polymerizable polysiloxanylalkyl-containing monomer, ethylenically unsaturated polymerizable monomer having ring-opening reactive functionalities, ethylenically unsaturated polymerizable nitrogen protected monomer with amino functionality in which all or a portion of the amino functionality is blocked with a nitrogen protecting group, and mixtures thereof.

9. The biomedical device of claim 8, wherein the ethylenically unsaturated polymerizable fluorine-containing monomer is selected from the group consisting of 2,2,2-trifluoroethyl(meth)acrylate, 2,2,3,3-tetrafluoropropyl(meth)acrylate, 2,2,3,3,3,-pentafluoropropyl(meth)acrylate, 1-trifluoromethyl-2,2,2-trifluoroethyl (meth)acrylate, 1H,1H,5H-octafluoropentyl(meth)acrylate, octafluoropentyl methacrylate, octafluoropentyl vinyl carbonate, octafluoropentyl n-vinyl carbamate, hexafluoroisopropyl(meth)acrylate, 2,2,3,3,4,4-hexafluorobutyl(meth)acrylate, pentafluorophenyl(meth)acrylate, pentafluorohexyl(meth)acrylate and mixtures thereof.

10. The biomedical device of claim 8, wherein the ethylenically unsaturated polymerizable fatty acid ester-containing monomer is selected from the group consisting of vinyl laurate, vinyl nonanoate, vinyl pivalate, vinyl crotonate, allyl crotonate, vinyl stearate and mixtures thereof.

11. The biomedical device of claim 8 wherein the ethylenically unsaturated polymerizable polysiloxanylalkyl-containing monomer is selected from the group consisting methacryloxypropyl tris(tnmethylsiloxy)silane, (trimethylsilyl) propyl vinyl carbonate; 3-(vinyloxycarbonylthio)propyl-[tris (trimethylsiloxy)silane]; 3-[tris(tri-methylsiloxy)silyl] propyl vinyl carbamate; 3-[tris(trimethylsiloxy)silyl]propyl allyl carbamate; 3-[tris(trimethylsiloxy)silyl]propyl vinyl carbonate, tris(trimethylsiloxy)silylpropyl methacrylamide, M1-MCR-C12 and mixtures thereof.

12. The biomedical device of claim 9, wherein the ethylenically unsaturated polymerizable monomer having ring-opening reactive functionalities is selected from the group consisting of glycidyl methacrylate, maleic anhydride, itaconic anhydride and mixtures thereof.

13. The biomedical device of claim 1, wherein the hydrophobic units are derived from a hydrophobic monomer selected from the group consisting of alkyl (meth)acrylates, N-alkyl(meth)acrylamides, alkyl vinylcarbonates, alkyl vinylcarbamates, fluoroalkyl(meth)acrylates, N-fluoroalkyl (meth)acrylamides, N-fluoroalkyl vinylcarbonates, N-fluoroalkyl vinylcarbamates, silicone-containing (meth)acrylates, (meth)acrylamides, vinyl carbonates, vinyl carbamates, vinyl esters, styrenic monomers, polyoxypropylene (meth) acrylates and mixtures thereof.

14. The biomedical device of claim 1, wherein the mixture further comprises a biomedical device-forming comonomer.

15. The biomedical device of claim 14, wherein the biomedical device-forming comonomer is a silicone-containing monomer.

16. The biomedical device of claim 1, wherein the mixture further comprises a hydrophilic monomer, hydrophobic monomer or both.

17. The biomedical device of claim 14, wherein the mixture further comprises a hydrophilic monomer selected from the group consisting of an unsaturated carboxylic acid, acrylamide, vinyl lactam, poly(alkyleneoxy)(meth)acrylate, (meth)acrylic acid, hydroxyl-containing-(meth)acrylate, hydrophilic vinyl carbonate, hydrophilic vinyl carbamate monomer, hydrophilic oxazolone monomer and mixtures thereof.

18. The biomedical device of claim 1, wherein the mixture further comprises a hydrophilic monomer selected from the group consisting of methacrylic acid, acrylic acid, 2-hydroxyethylmethacrylate, 2-hydroxyethylacrylate, N-vinyl pyrrolidone, methacrylamide, N,N-dimethylacrylamide, ethylene glycol dimethacrylate and mixtures thereof.

19. The biomedical device of claim 1, wherein the device is a contact lens.

20. The biomedical device of claim 19, wherein the contact lens is a rigid gas permeable contact lens.

21. The biomedical device of claim 19, wherein the contact lens is a soft contact lens.

22. The biomedical device of claim 19, wherein the contact lens is a hydrogel contact lens.

23. The biomedical device of claim 1, wherein the device is an intraocular lens.

24. The biomedical device of claim 1, wherein the device is a corneal implant.

* * * * *